United States Patent
Choi et al.

(10) Patent No.: US 6,602,818 B2
(45) Date of Patent: *Aug. 5, 2003

(54) METHOD FOR PREPARING A CATALYST FOR SELECTIVE CATALYTIC REDUCTION OF NITROGEN OXIDES

(75) Inventors: Kyung-Il Choi, Taejon (KR); Sang-Ho Lee, Taejon (KR); Choul-Woo Shin, Taejon (KR); Jun-Seong Ahn, Taejon (KR)

(73) Assignee: SK Corporation, Seoul (KR)

(*) Notice: Subject to any disclaimer, the term of this patent is extended or adjusted under 35 U.S.C. 154(b) by 0 days.

This patent is subject to a terminal disclaimer.

(21) Appl. No.: 09/963,272

(22) Filed: Sep. 25, 2001

(65) Prior Publication Data
US 2002/0058586 A1 May 16, 2002

(30) Foreign Application Priority Data
Sep. 27, 2000 (KR) .................. 2000-56679

(51) Int. Cl.$^7$ .................. B01J 27/051; B01J 27/047; B01J 21/08; B01J 23/00; B01J 23/20
(52) U.S. Cl. .................. 502/220; 502/219; 502/221; 502/222; 502/242; 502/245; 502/246; 502/247; 502/248; 502/258; 502/259; 502/308; 502/315; 502/305; 502/309; 502/312; 502/313; 502/323; 502/325; 502/354; 502/506; 502/514
(58) Field of Search .................. 502/219–222, 502/242, 245–248, 258, 259, 308, 315, 305, 309, 312, 313, 323, 325, 354, 506, 514

(56) References Cited

U.S. PATENT DOCUMENTS

| 5,827,489 A | 10/1998 | Garcin et al. ............ 423/239.1 |
| 6,171,566 B1 | 1/2001 | Ku et al. ............ 423/239.1 |

*Primary Examiner*—Mark L. Bell
*Assistant Examiner*—Patricia L. Hailey
(74) *Attorney, Agent, or Firm*—Abelman, Frayne & Schwab

(57) ABSTRACT

Disclosed are a catalyst for selective catalytic reduction of nitrogen oxides and a method for preparing the same. The catalyst is prepared using a spent catalyst discharged from a hydro-desulfurization process of an oil refinery in which the spent catalyst comprises vanadium, nickel, molybdenum and sulfur component on alumina, and a tungsten-impregnated support. The catalyst prepared in accordance with the present invention is very advantageous in terms of excellent selective removal effect of nitrogen oxides as well as better poisoning resistance to sulfur oxides.

14 Claims, 1 Drawing Sheet

METHOD FOR PREPARING A CATALYST FOR SELECTIVE CATALYTIC REDUCTION OF NITROGEN OXIDES

BACKGROUND OF THE INVENTION

1. Field of the Invention

The present invention pertains, in general, to a catalyst for selective catalytic reduction of nitrogen oxides and a method for preparing the same. More specifically, the present invention pertains to a preparation of a catalyst for selective catalytic reduction of nitrogen oxides having excellent removal efficiency of nitrogen oxides, a thermal stability at high temperatures, and chemical stability and poisoning resistance to various inorganic, organic dusts and sulfur compounds contained in an exhaust gas, which is prepared by recycling an alumina-based spent catalyst discharged from a hydro-desulfurization process of an oil refinery.

2. Description of the Prior Art

Generally, nitrogen oxides ($NO_x$) are inevitably generated by plants which consume fossil fuels, such as power plants and chemical plants. Nitrogen oxides are found to be an immediate cause of the pollution, such as acid rain and smog. Now, most countries including Korea strictly forbid the discharge of nitrogen oxides above the allowed standard levels. Accordingly, a technique for removing nitrogen oxides from waste gas in a combustion system has been devised.

Meanwhile, to eliminate the source of nitrogen oxides emissions, which are produced by a reaction of nitrogen and oxygen in the presence of excess air in high temperature combustion equipment, there have been made many attempts for the improvement of the combustion conditions, such as low oxygen combustion and exhaust gas circulation. However, the nitrogen oxides cannot be completely eliminated only by improvements in combustion technique and thus, there are developed and suggested various post-treatment techniques by which the exhaust gas may be deprived of nitrogen oxides.

Techniques for effectively eliminating nitrogen oxides ($NO_x$) are commonly classified into a selective catalytic reduction (SCR) using a catalyst and a reductant together, a selective non-catalytic reduction (SNCR) using only a reductant without a catalyst, a low-$NO_x$ burner technique controlling a combustion state in the burner and so on. Among them, the selective catalytic reduction is valued as an effective technique for removing nitrogen oxides, taking notice of the generation of secondary pollution, removal efficiency, operation cost, etc. By using the selective catalytic reduction technique, nitrogen oxides may be removed with an efficiency of 90% or greater and the endurance period thereof may be used for about 2–5 years. In addition, said technique is technically advantageous because poisonous dioxin may be removed, along with nitrogen oxides, in the incinerator.

Catalysts useful in the selective catalytic reduction are classified into an extruded honeycomb catalyst, a metal plate catalyst, and a pellet catalyst, depending on their external forms. Currently, the extruded honeycomb and the metal plate catalysts are widely used in steam powder plants and incinerators. Useful as a support of the catalysts are titania, alumina, silica, zirconia and so on, and the catalyst composition mainly comprises oxides of active metals such as vanadium, molybdenum, nickel, tungsten, iron, and copper, and further comprises other active metal components for broadening temperature ranges and enhancing durability of the catalyst.

It became recently known that a catalyst for selective catalytic reduction can be manufactured containing oxides of crystalline phases by impregnating a support of inorganic oxides such as titania, alumina, silica and zirconia with catalytic components such as vanadium, molybdenum, nickel and tungsten, followed by thermal treatment.

In this regard, U.S. Pat. No. 5,827,489 discloses a process for the preparation of a catalyst for selective catalytic reduction containing oxides of crystal phases by impregnating a support of inorganic oxides such as titania, alumina, silica and zirconia with catalytic components such as vanadium, molybdenum, nickel and tungsten, thereafter heat treating. This patent employs a support and catalytic components with a superior poisoning resistance to sulfur oxides for the selective catalytic reduction and has advantages of freely controlling the amounts of active metals, a specific surface area and pore sizes of the catalyst to prepare the catalyst having optimal performance in which a suitable amount of sulfate is added. On the other hand, it suffers from high preparation cost because each of single materials (or precursors) used as the support and the catalyst should be prepared by methods of catalyst production and mixing.

Meanwhile, oil refineries essentially employ a hydro-desulfurization process for removing sulfur components contained in crude oil, from which a spent catalyst is discharged as a by-product. However, if such a spent catalyst is not recycled, treatment cost therefore are required continuously, which is disadvantageous in the economic aspect:

In this regard, Korean Patent Laid-Open No. 95-72277 and U.S. Pat. No. 6,171,566 refer to recycling of spent catalysts discharged from a hydro-desulfurization process of an oil refinery. A catalyst for selective catalytic reduction prepared by recycling such spent catalysts is more advantageous in terms of low preparation cost, inherent poisoning resistance to sulfur oxides, and containing the high content of metal components with excellent activities for nitrogen oxides reduction, compared with a catalyst prepared by a combination process of single materials.

However, when a spent catalyst is used alone in the selective catalytic reduction of nitrogen oxides, the active metal components contained therein are not uniformly impregnated within pores of support, or on its surface, but present in lump form, thereby lowering catalytic performance. The above patent suffers from the disadvantages that catalytically active components are impregnated at excessive levels rather than required. Further, a small amount of other metal components and an excess amount of sulfur compounds which decreases catalytic performance are present, and also the spent catalyst discharged from different discharge-lines after a hydro-desulfurization process has different properties, and thus it is difficult to apply to commercial catalytic processes. In the case of using the pretreated spent catalyst alone in the preparation of a catalyst for selective catalytic reduction of nitrogen oxides, thusly prepared catalyst does not exhibit sufficiently satisfactory performance. Also, because the support in the spent catalyst mainly comprises alumina, poisoning may occur by a physical adsorption or a chemical reaction when the catalyst is employed in the application in which sulfur components and oil sludge are discharged at a large amount.

SUMMARY OF THE INVENTION

Leading to the present invention, the intensive and thorough research on a spent catalyst discharged from a hydro-desulfurization process of an oil refinery, carried out by the present inventors aiming to avoid the problems encountered in the prior arts, resulted in the finding of a method for preparing a catalyst for selective catalytic reduction of nitrogen oxides in the form of a catalyst body having excellent performance and durability, and low preparation cost from the spent catalyst.

Therefore, it is an object of the present invention to provide a method for preparing a catalyst for selective catalytic reduction of nitrogen oxides, which has excellent removal effect of nitrogen oxides and poisoning resistance.

It is another object of the present invention to provide a method for preparing a catalyst for selective catalytic reduction of nitrogen oxides by recycling a spent catalyst discharged from a hydro-desulfurization process of an oil refinery.

It is a further object of the present invention to provide a catalyst for selective catalytic reduction of nitrogen oxides prepared by recycling a spent catalyst discharged from a hydro-desulfurization process of an oil refinery.

In accordance with the present invention, there is provided a method for preparing a catalyst for selective catalytic reduction of nitrogen oxides comprising the following steps:

a) pretreating a spent catalyst discharged from a hydro-desulfurization process of an oil refinery, comprising 1 to 30 wt % of vanadium, 1 to 20 wt % of nickel, 1 to 20 wt % of molybdenum and 1 to 15 wt % of sulfur component on alumina, by thermally treating said spent catalyst followed by washing with water
   b) providing a support impregnated with 1 to 15 wt % of tungsten on the support basis, said support being selected from the group consisting of alumina, titania, silica, zeolite and a mixture thereof;
   c) pulverizing the pretreated spent catalyst, followed by homogeneously wet-mixing the pulverized spent catalyst with the tungsten-impregnated support under the addition of water and acid;
   d) dehydrating the mixture to remove excess moisture and non-impregnated active metals therein;
   e) drying the dehydrated mixture, followed by grinding the dried mixture; and
   f) extruding the grinded mixture or coating the grinded mixture to a structure, followed by drying and then calcining to form a catalyst body.

BRIEF DESCRIPTION OF THE DRAWING

The above and other objects, features and other advantages of the present invention will be more clearly understood from the following detailed description taken in conjunction with the accompanying drawing.

DETAILED DESCRIPTION OF THE INVENTION

Figure 1:
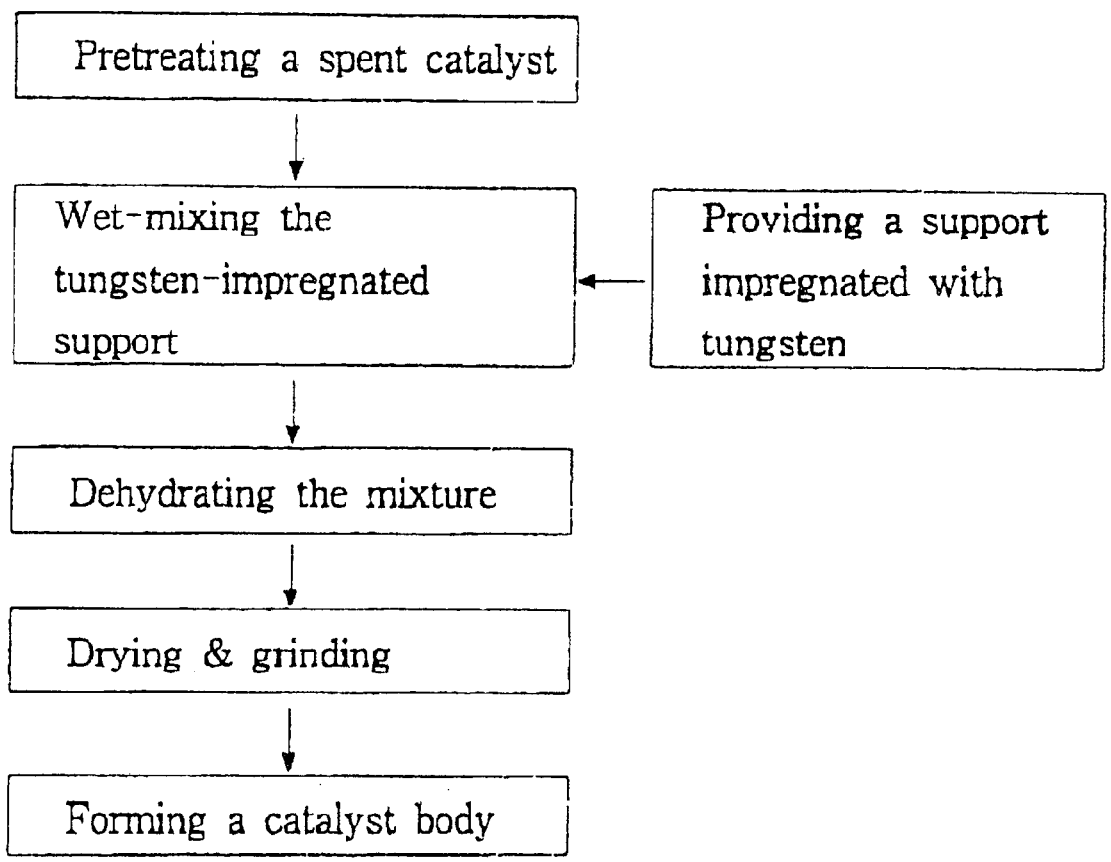
FIG. 1 shows a diagram of processes for preparing a catalyst for selective catalytic reduction of nitrogen oxides using a spent catalyst according to the present invention.

A "catalyst" for selective catalytic reduction of nitrogen oxides according to the present invention should have desired levels of active metal contents, a defined specific surface area and pore size of its support, and also exhibit excellent performance under severe test conditions. Generally, a catalyst having an excess amount of the active metals and a small specific surface area has excellent removal efficiency of nitrogen oxides but narrow active temperature ranges. On the other hand, in the case of a catalyst having a small amount of active metals and large specific surface area, the removal efficiency of nitrogen oxides becomes low and the active temperature range is broadened to high temperatures.

Referring to FIG. 1, there is shown a process of preparation of a catalyst for selective catalytic reduction of the present invention.

In the present invention, use may be made of a spent catalyst discharged from a hydro-desulfurization process of an oil refinery. The spent catalyst comprises 1–30 wt % of vanadium, 1–20 wt % of nickel, 1–20 wt % of molybdenum and 1–15 wt % of sulfur component on an alumina support, which has a specific surface area of 30–200 $m^2/g$ and pore sizes of 100–300 Å.

In general, the surface of the spent catalyst is contaminated with oils, carbon and a part of sulfur in combination with various impurities during the hydro-desulfurization process. To eliminate such components, the spent catalyst is thermally treated preferably at 300–400° C. for 3–5 hours. At this thermal treatment temperature, which is the standard processing condition, carbon and a part of sulfur (especially, carbon) may be effectively eliminated. Thereafter, the thermally treated spent catalyst is washed with water, preferably, for about 1 hour in an batch-typed aeration bath to remove sulfur components and excess metal components accumulated in the spent catalyst to a certain extent. To facilitate removing excess metal components, the spent catalyst may be optionally treated with acids such as oxalic acid.

Separately from the above pretreating step, a support impregnated with tungsten is prepared and provided. Such support is selected from the group consisting of alumina, titania, silica, zeolite and a mixture thereof, which has large specific surface area. In the tungsten-impregnated support, tungsten is impregnated at an amount of 1–15 wt % on the support basis. In particular, it is preferred that gamma alumina is used as said alumina and the titania having anatase crystalline structure is used. As such, the tungsten-impregnated support has the specific surface area of 50–400 $m^2/g$ and the pore size of 150–250 Å.

The pretreated spent catalyst is pulverized in the form of powders to be suitable for the homogeneous mixing in the subsequent step.

The pulverized catalyst as above is wet-mixed with the above tungsten-impregnated support under the addition of water and acid. While passing through said wet mixing step, the active metal components contained in the spent catalyst are dissolved out and then homogeneously impregnated to the tungsten-impregnated support. At this time, a wet-mixing ratio of the spent catalyst to the tungsten-impregnated support is preferably 50:50–70:30 on a weight basis. When the amount of the spent catalyst is less than 50 wt %, the amount of active metal components is too low and the specific surface area becomes excessively large. On the other hand, when the spent catalyst exceed 70 wt %, an excess amount of the metal component is present in the mixture and also the specific surface area becomes too low.

Said pulverizing and wet-mixing steps may be conducted using a ball mill reactor for about 3–4 hours. During the wet-mixing step, suitable amounts of water and acid are added to obtain a mixture of slurry state.

In general, large quantities of the active metal components in lump form, heterogeneously impregnated within pores or on the surface of the alumina, are present in the spent catalyst. In accordance with the present invention, the acid is used for dissolving excess metal components contained in the spent catalyst. Such dissolved active metals are re-distributed into the tungsten-impregnated support. In other words, active metal components are dissolved in acids so that the alumina of the spent catalyst has much larger specific surface area and excess active metals are adsorbed into pores in the tungsten-impregnated support with large specific surface area. The acids should dissolve active metals such as vanadium, nickel, molybdenum, and organic components. As such, the acids are used at a suitable amount because excess addition of the acids results in dissolving the alumina support as well as metals. Such acids are exemplified by oxalic acid and added preferably at an amount of 1–5 wt % on the basis of the spent catalyst, depending on metal components contained in the spent catalyst.

After the wet-mixing step, the slurry mixture is uniformly dehydrated under a pressure of about 15 kg/cm$^2$ by use of a filter press to eliminate excess moisture and metal components, thereby yielding a dehydrated cake.

The dehydrated mixture is dried preferably at 100–200° C. to remove moisture therein, which is suitable for the preparation of the catalyst body. The dried mixture is grinded to a suitable size for the preparation of the catalyst body in the extruded form or in the form of a structure coated therewith, preferably 200 μm or less.

The dried and grinded mixture as above may be extruded, preferably in the form of a honeycomb, or coated to a structure, dried preferably at 100–120° C. and then calcined preferably at 450–550° C. for 3 hours or more, thereby yielding a catalyst in the form of a catalyst body. It is preferred that sparkling metals, for example in the form of metal plate, or ceramics, for example cordierite as said structure are used.

In accordance with the present invention, it is preferred that the catalyst for selective catalytic reduction of nitrogen oxides prepared as above comprises metal components containing 1 to 10 wt % of vanadium, 1 to 10 wt % of nickel, 1 to 10 wt % of molybdenum and 1 to 15 wt % of tungsten in the form of oxide, 1 to 10 wt % of sulfur components, and a support comprising alumina or a mixture of alumina and one selected from the group consisting of titania, silica, zeolite and a mixture thereof. Further, the catalyst has a specific surface area of 50 to 150 m$^2$/g and a pore size of 150 to 250 Å.

A better understanding of the present invention may be obtained in light of the following examples which are set forth to illustrate, but are not to be construed to limit the present invention.

COMPARATIVE EXAMPLE 1

A spent catalyst having a specific composition, discharged from a hydro-desulfurization process of an oil refinery, was thermally treated at 400° C. for 3 hours to remove carbon and sulfur compounds therein and washed with water to remove excess active metal components and sulfur compounds therein. Thereafter, the spent catalyst is dried at 100° C. for 3 hours and calcined at 450° C. for 3 hours, which is referred to as "Catalyst A". The Catalyst A was analyzed for its composition using XRF and ICP method and the result thereof was shown in Table 1, below.

The performance test for the nitrogen oxide reduction catalytic activity of Catalyst A was conducted in the presence of 500 ppm nitrogen monoxide (NO) and 500 ppm ammonia (NH$_3$), under severe conditions of a gaseous hourly space velocity of 100,000/hr, and reaction temperature was increased at a rate of 5° C./min. in the range of 30° C. to 500° C. The result is presented in Table 1, below.

EXAMPLE 1

500 g of the same spent catalyst as in Comparative Example 1 was thermally treated at 400° C. for 3 hours and treated with 500 g of water. The spent catalyst as treated above was dried at 100° C. for 3 hours, and then pulverized.

Ammonium meta tungstate was added to Meta titanic acid slurry with solid content of 20–25 wt %, admixed homogeneously, in which the ammonium meta tungstate was added at an amount of 5 wt % on the basis of the solid weight of the slurry, and thereafter, thermally treated at 550° C. for 2 hours. The tungsten-impregnated titania support was founded to have a specific surface area of 100 m$^2$/g by BET method and anatase crystalline structure.

350 g of the pulverized spent catalyst and 150 g of the tungsten-impregnated titania was wet-mixed in the ball mill reactor under addition of 500 g of water and 8 g of oxalic acid. Next, the mixture was filter pressed under 15 kg/cm$^2$, dried at 120° C. for 24 hours, and grinded to a particle size of 150 μm. Thereafter, calcination was carried out at 450° C. for 3 hours to give a catalyst in the powder form, which is referred to as "Catalyst B". The analysis for composition and the performance test for the nitrogen oxide reduction catalytic activity were conducted in the same manner as Comparative Example 1. The results are presented in Table 1, below.

EXAMPLE 2

Catalyst C was prepared in the same manner as Example 1, except that 250 g of the pulverized spent catalyst and 250 g of the tungsten-impregnated titania was wet-mixed.

The analysis for composition and the performance test for the nitrogen oxide reduction catalytic activity were conducted in the same manner as Comparative Example 1. The results are presented in Table 1, below.

TABLE 1

| Catalyst | Components (wt %) | | | | | | Catalyst Property Specific surface area (m²/g) | Catalyst Performance | |
| --- | --- | --- | --- | --- | --- | --- | --- | --- | --- |
| | V | Ni | Mo | S | Al | Ti + W | | Maximum Activity (%) | Activity Range (° C.)[1] |
| A | 9.2 | 4.7 | 3.9 | 4.2 | 33.1 | — | 72 | 84 | — |
| B | 6.5 | 1.4 | 2.9 | 2.3 | 26.5 | 19.5 | 81 | 98 | 230–330 |
| C | 4.6 | 1.0 | 1.1 | 2.2 | 19.6 | 31.8 | 84 | 100 | 210–450 |

Note:
[1] range having activity of 90% or higher

As can be seen in the above table, the catalysts B and C have more excellent catalytic performance and broader temperature range than those of the catalyst A.

EXAMPLE 3 to 5

Catalyst D, E and F were prepared the same procedure as Example 1, except employing alumina having a specific surface area of 200 (Example 3), silica having a specific surface area of 300 (Example 4) and zeolite having a specific surface area of 300 (Example 5), respectively, instead of titania as a support for impregnating tungsten.

The analysis for composition of Catalyst D, E and F, respectively was conducted using XRF and ICP method and the results thereof are shown in Table 2, below.

The performance tests of Catalyst D, E and F were conducted in the presence of 500 ppm nitrogen monoxide (NO) and 500 ppm ammonia ($NH_3$), under severe conditions of a gaseous hourly space velocity of 100,000/hr, and reaction temperature was increased at a rate of 5° C./min. in the range of 30° C. to 500° C. The results are given in Table 2, below.

TABLE 2

| Catalyst | Components (wt %) | | | | | | Catalyst Property | Catalyst Performance | |
| --- | --- | --- | --- | --- | --- | --- | --- | --- | --- |
| | V | Ni | Mo | S | Al | Additional support + Tungsten | Specific surface area (m²/g) | Maximum Activity (%) | Activity Range (° C.)[1] |
| D[2] | 6.5 | 1.4 | 2.9 | 2.3 | 26.5 | 19.4 | 88 | 95 | 320–400 |
| E[3] | 6.5 | 1.4 | 2.9 | 2.3 | 26.5 | 19.5 | 92 | 92 | 330–410 |
| F[4] | 6.5 | 1.4 | 2.9 | 2.3 | 26.5 | 19.3 | 97 | 93 | 330–430 |

Note:
[1] range having activity of 90% or higher;
[2] additional support is alumina;
[3] additional support is silica; and
[4] additional support is zeolite.

From the results of the above table, it can be seen that the Catalysts D, E and F have excellent catalytic performance over a broad temperature range.

COMPARATIVE EXAMPLE 2

A material for a catalyst body was prepared in the same manner as Catalyst A in Comparative Example 1, except that calcination was not carried out. 46 wt % of the material, 42 wt % of water, 1 wt % of light mineral oil, 4 wt % of methyl cellulose, 3 wt % of glass fiber and 4 wt % of Kaolinite were mixed, kneaded, and extruded into a honeycomb having 25 cells. The honeycomb was dried 120° C. for 24 hours and calcined at 450° C. for 3 hours to give Catalyst G, which is analyzed for its composition using XRF and ICP method.

The performance test for the nitrogen oxide reduction catalytic activity of Catalyst G was conducted in the presence of 500 ppm nitrogen monoxide (NO) and 500 ppm ammonia ($NH_3$), under severe conditions of a gaseous hourly space velocity of 5,000/hr, and reaction temperature was increased at a rate of 5° C./min. in the range of 30° C. to 500° C. The results are shown in Table 3 below.

EXAMPLE 6

A mixture material for a catalyst body was prepared in the same manner as Catalyst B in Example 1, except that calcination was not carried out. The mixture material was formed into a honeycomb to give Catalyst H, and the composition analysis and performance test were conducted in the same manner as Comparative Example 2. The results are given in Table 3, below.

EXAMPLE 7

A mixture material for a catalyst body was prepared in the same manner as Catalyst C in Example 2, except that calcination was not carried out. The mixture material was formed into a honeycomb to give Catalyst I, and the composition analysis and performance test were conducted in the same manner as Comparative Example 2. The results are given in Table 3, below.

TABLE 3

| | Components (wt %) | | | | | | Catalyst Property | Catalyst Performance | |
| | | | | | | | Specific surface area | Maximum Activity | Activity Range |
| Catalyst | V | Ni | Mo | S | Al | Ti | W | (m²/g) | (%) | (° C.)[1] |
|---|---|---|---|---|---|---|---|---|---|---|
| G | 9.0 | 4.5 | 3.3 | 3.6 | 32.0 | — | — | 70.0 | 82 | — |
| H | 6.3 | 1.2 | 2.7 | 3.6 | 25.1 | 15.3 | 1.0 | 79.5 | 95 | 280–380 |
| I | 4.1 | 1.0 | 1.3 | 3.6 | 17.7 | 26.2 | 1.7 | 83.5 | 98 | 270–430 |

Note:
[1] range having activity of 90% or higher;

As aforementioned, a catalyst for selective catalytic reduction of nitrogen oxides prepared in accordance with a method of the present invention, has an excellent removal effect of nitrogen oxides and poisoning resistance to sulfur oxides. In addition, a spent catalyst can be recycled so that economic favor occurs.

The present invention has been described in an illustrative manner, and it is to be understood that the terminology used is intended to be in the nature of description rather than of limitation. Many modifications and variations of the present invention are possible in light of the above teachings. Therefore, it is to be understood that within the scope of the appended claims, the invention may be practiced otherwise than as specifically described.

What is claimed is:

1. A method for preparing a catalyst for selective catalytic reduction of nitrogen oxides, comprising the following steps of:
   a) pretreating a spent catalyst discharged from a hydrodesulfurization process of an oil refinery, comprising 1 to 30 wt % of vanadium, 1 to 20 wt % of nickel, 1 to 20 wt % of molybdenum and 1 to 15 wt % of sulfur component on alumina, by thermally treating said spent catalyst followed by washing with water
   b) providing a support impregnated with 1 to 15 wt % of tungsten on the support basis, said support being selected from the group consisting of alumina, titania, silica, zeolite and a mixture thereof;
   c) pulverizing the pretreated spent catalyst, followed by homogeneously wet-mixing the pulverized spent catalyst with the tungsten-impregnated support under the addition of water and acid;
   d) dehydrating the mixture to remove excess moisture and non-impregnated active metals therein;
   e) drying the dehydrated mixture, followed by grinding the dried mixture; and
   f) extruding the grinded mixture or coating the grinded mixture to a structure, followed by drying and then calcining to form a catalyst body.

2. The method as defined in claim 1, wherein the spent catalyst has a specific surface area of 30 to 200 m²/g and a pore size of 100 to 300 Å.

3. The method as defined in claim 1, wherein the tungsten-impregnated support to be mixed with the spent catalyst, has a specific surface area of 50 to 400 m²/g and a pore size of 150 to 250 Å.

4. The method as defined in claim 1, wherein the alumina support provided in the b) step is made of a gamma alumina.

5. The method as defined in claim 1, wherein the titania support provided in the b) step has an anatase crystalline structure.

6. The method as defined in claim 1, wherein a mixing ratio of the spent catalyst to the tungsten-impregnated support in the c) step ranges 50:50 to 70:30 on the weight basis.

7. The method as defined in claim 1, wherein the acid in the c) step is oxalic acid and used at an amount of 1–5 wt % on the basis of the spent catalyst.

8. The method as defined in claim 1, wherein the structure is made of sparkling metals or ceramics.

9. The method as defined in claim 1, wherein the thermally treating of the a) step is carried out at 300 to 400° C. for 3–5 hours.

10. The method as defined in claim 1, wherein drying of the f) step is carried out at 100 to 120° C.

11. The method as defined in claim 1, wherein calcining of the f) step is carried out at 450 to 550° C. for 3 hours or more.

12. A catalyst for selective catalytic reduction of nitrogen oxides prepared according to claim 1.

13. The catalyst as defined in claim 12, wherein the catalyst comprises metal components containing 1 to 10 wt % of vanadium, 1 to 10 wt % of nickel, 1 to 10 wt % of molybdenum and 1 to 15 wt % of tungsten in the form of oxide; 1 to 10 wt % of sulfur components; and a support comprising alumina or a mixture of alumina and one selected from the group consisting of titania, silica, zeolite and a mixture thereof.

14. The catalyst as defined in claim 12, wherein the catalyst has a specific surface area of 50 to 150 m²/g and a pore size of 150 to 250 Å.

* * * * *